Figure 1:
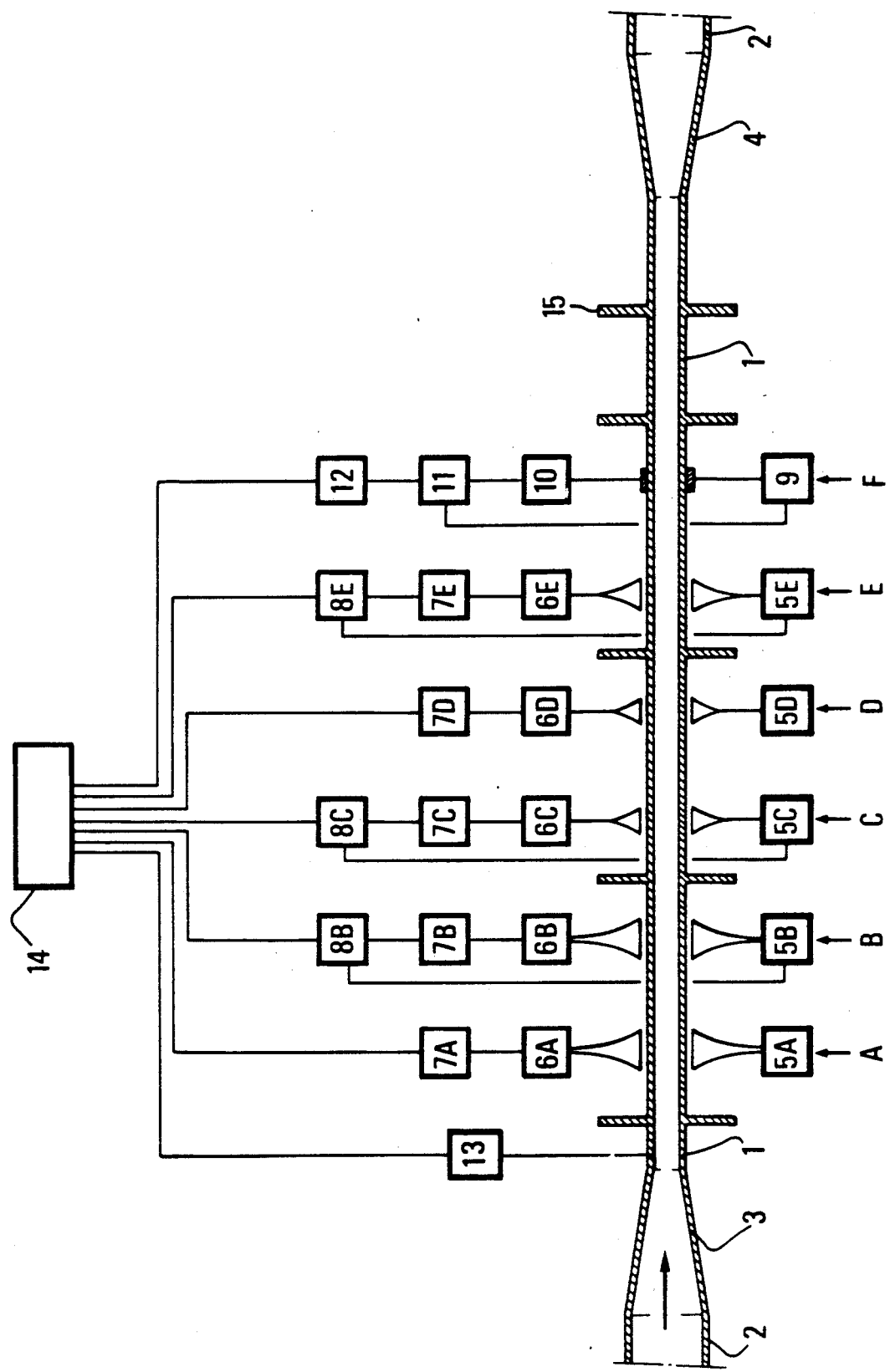

United States Patent [19]

Castel et al.

[11] Patent Number: 5,049,823
[45] Date of Patent: Sep. 17, 1991

[54] METHOD AND DEVICE FOR MEASURING THE QUALITIES OF A MULTIPHASE FLUID

[75] Inventors: Yvon Castel, Croissy Sur Seine; John Lynch, Rueil-Malmaison; Jean-Pierre Burzynski, Lyons, all of France

[73] Assignee: Institut Francais du Petrole, Rueil-Malmaison, France

[21] Appl. No.: 527,340

[22] Filed: May 23, 1990

[30] Foreign Application Priority Data

May 23, 1989 [FR] France ................................. 89 06835

[51] Int. Cl.⁵ ........................................... G01N 22/00
[52] U.S. Cl. ................................. 324/640; 73/61.1 R; 73/861.04
[58] Field of Search ............. 73/61.1 R, 61 R, 861.04, 73/861.08; 324/640

[56] References Cited

U.S. PATENT DOCUMENTS

| | | | |
|---|---|---|---|
| 4,423,623 | 1/1984 | Ho et al. .............................. | 73/61 R |
| 4,812,739 | 3/1989 | Swanson ............................. | 324/640 |
| 4,820,970 | 4/1989 | Swanson ............................. | 324/640 |
| 4,852,395 | 8/1989 | Kolpak ............................. | 73/61.1 R |
| 4,888,547 | 12/1989 | McGinn et al. ............. | 73/61.1 R X |
| 4,891,769 | 1/1990 | Wayland et al. ................ | 73/61.1 R |
| 4,902,961 | 2/1990 | De et al. ....................... | 73/61.1 R X |

Primary Examiner—Hezron E. Williams
Assistant Examiner—Joseph W. Roskos
Attorney, Agent, or Firm—Antonelli, Terry, Stout & Kraus

[57] ABSTRACT

A method and a device for measuring the qualities of a fluid including at least two liquids, the two liquids having at least one characteristic intrinsic factor relative to microwaves for a given frequency, such as the loss factor. The characteristic of the fluid is measured by a microwave flux for at least two different microwave frequencies, and, with the values of the factors of the intrinsic characteristics of each of the fluids at the two frequencies being known, the respective quantities of the two liquids are determined. The invention applies in particular to measuring the concentrations and flowrates of various phases in a multiphase fluid such as a petroleum effluent having an aqueous phase.

17 Claims, 2 Drawing Sheets

METHOD AND DEVICE FOR MEASURING THE QUALITIES OF A MULTIPHASE FLUID

The invention relates to a device and a method for measuring the qualities of a fluid, comprising at least two liquids, by means in particular of microwaves, whereby these qualities may be the quantities of the two liquids, their speed, their flowrate, or the quantity or speed of a gas contained in the fluid.

The invention applies in particular to production of hydrocarbons containing a multiphase gas-liquid mixture, which production may in particular, but not exclusively, be effected in a setting to which access is difficult, for example at a wellhead or the head of an undersea pipeline, or in a virgin forest.

The invention also applies to the chemical and oil industries, or in general to all industries employing fluids containing at least two liquids, whether or not these liquids are miscible.

In oil production in particular, the attempt is generally made to discover the quantities of flowrates of the three components—water, liquid hydrocarbons, and gas—which constitute three separate phases whose qualities are difficult to analyze continuously.

It is known that neutron bombardment, gamma radiation (dichromic), microwaves, and nuclear magnetic resonance may be used to measure the concentration of a single liquid in a fluid comprising several liquids. Moreover, classical measuring techniques employing microwaves can determine only the concentration of a liquid having high absorption by comparison to another liquid with which it is mixed.

The method and the device according to the present invention allow the absolute and relative quantities of at least two liquids contained in a fluid to be measured.

In carrying out the measurements, at least one intrinsic characteristic of the fluids relative to microwaves is used. This characteristic, which may be absorption, reflection, diffusion, diffraction, polarization, phase shift of microwaves, is defined by a factor. This factor depends on the characteristics of the microwave beam, for example the frequency or frequencies of this beam, and of the fluid or more generally the body traversed. Advantageously, the characteristic measured is absorption and the factor is, for example, the microwave absorption factor which is called a microwave loss factor or loss factor. This factor can be measured by transmission or by transmission and reflection.

Microwaves are understood to be waves with a frequency of between 0.1 and 1000 GHz, but advantageously for implementation of the method or construction of the device according to the invention, the microwave frequency used is between 1 and 100 GHz, or between 10 and 100 GHz.

The invention proposes a method for measuring the qualities of a fluid comprising at least two liquids, the two liquids having at least one factor of a characteristic intrinsic to microwaves for a given frequency, one of the two liquids being a first liquid and the other liquid being a second liquid. This method is characterized in particular by measuring the characteristic of the fluid by a microwave flux for at least two different microwave frequencies, and, with the values of the factors of the intrinsic characteristics of each of the fluids at the two frequencies being known, the respective quantities of the two liquids are determined, one of the two frequencies being hereinafter called the first frequency and the other the second frequency.

Other frequencies different from the first and second frequencies, having either the properties of the first frequency or those of the second frequency, may refine the accuracy of the measurements sought.

The factor of the intrinsic characteristic may be the microwave loss factor, and the intrinsic characteristic will be absorption with respect to microwaves.

The fluid may comprise gas.

In the case where, for the first frequency, the first liquid has an intrinsic characteristic factor that is negligible by comparison with the intrinsic characteristic factor of the second liquid, the second frequency being a frequency at which the intrinsic characteristic factor of the first liquid is not negligible by comparison with the intrinsic characteristic factor of the second liquid, the quantity of the second liquid may be determined by measuring the microwave flux characteristic through the liquid at the first frequency, neglecting the intrinsic characteristic factor of the first liquid by comparison to the characteristic factor of the second liquid.

When the second liquid includes an aqueous compound, the first frequency may be close to 21 GHz and the second frequency may be remote from 21 GHz. "Remote frequency" is understood to be the frequency above which the instrument measuring the microwave flux characteristic is capable of detecting a given quantity of the first liquid.

The first liquid may include a hydrocarbon compound.

If the fluid is moving in one direction, the variation in frequency of a microwave flux with an initial frequency traversing the fluid in a direction not perpendicular to the direction of movement can be measured, the initial frequency being a frequency for which the intrinsic characteristic factor of the first or second liquid is negligible by comparison to the intrinsic characteristic factors of the second or first liquid respectively, and the velocity of the liquid whose intrinsic characteristic factor is preponderant can be measured.

When the fluid is moving, the change as a function of time in the amplitude of a microwave flux having at least one initial frequency and traversing the fluid in a direction not perpendicular to the direction of movement can be determined, the initial frequency being a frequency for which the intrinsic characteristic factors of the first and second fluid are of the same order of magnitude, then a frequency analysis may be made of the changes in the amplitude in order to establish at least one frequency variation, and from the variation or variations in initial frequency and the composition of the fluid, the velocity of each of the liquids of the fluid may be determined.

When the fluid includes a moving gas, the gas having particles with which factor of an intrinsic characteristic relative to microwaves is associated, at least part of the gas and the liquids can be separated, the variation in frequency of microwave flux having an initial frequency and traversing the gas part in a direction not perpendicular to the movement can be measured, and the velocity of the gas can be determined from the variation in frequency.

The initial frequency of the microwave flux traversing the fluid may be chosen such that the intrinsic characteristic factor of the first or second liquid is negligible by comparison to the intrinsic characteristic factor of the second or the first liquid, respectively.

The fluid could be disposed in a volume having two parallel faces, and the characteristic of the microwave flux traversing at least part of the parallel faces can be detected or measured.

The invention also proposes a device for measuring the qualities of a fluid.

This device is characterized in particular by having a volume to hold the liquid which has two parallel windows transparent to microwaves, and by having a microwave transmitter for microwaves that pass through one or the first of the windows, and a microwave receiver sensitive to microwaves that have passed through the first and the second window.

These windows may be disposed on either side of the volume such that the volume is traversed through and through, for example in direct transmission measurements.

These windows may be disposed on the same side of the volume, for example when measurements are to be made by reflection or transmission-reflection.

The windows may be made of a composite material transparent to microwaves.

When the fluid is flowing, the volume of the device may be a section of pipe.

The invention is based in particular on the following principles:

the intrinsic characteristic factor, such as the loss factor for absorption, depends both on the material, such as the fluid, and on the frequency at which this factor is measured;

the factor generally varies a great deal with the frequency and has an extreme which is a maximum for a given frequency and which depends on the material. Hence, when a fluid which has at least two liquids whose intrinsic characteristic factors are different, is to be analyzed, a characteristic such as absorption is measured for at least two frequencies chosen to permit discrimination between the various factors of the characteristics at these two frequencies. Preferably, one or, even better, both frequencies are chosen as being frequencies at which one of the factors is negligible by comparison to the other.

For example, in a mixture of water and hydrocarbon oil, the measuring frequency is chosen at about 21 GHz since, for the absorption being measured, the loss factor of water is about 30 to 40, while the loss factor of oil is bout $10^{-6}$. In this case, the ratio between the absorption factors is about $3 \cdot 10^7$.

Hence, measurement of absorption at this frequency furnishes the water content of the fluid.

Once its water content is known, one need then only measures the absorption of the fluid at another frequency and determine the oil content.

Figure 2:
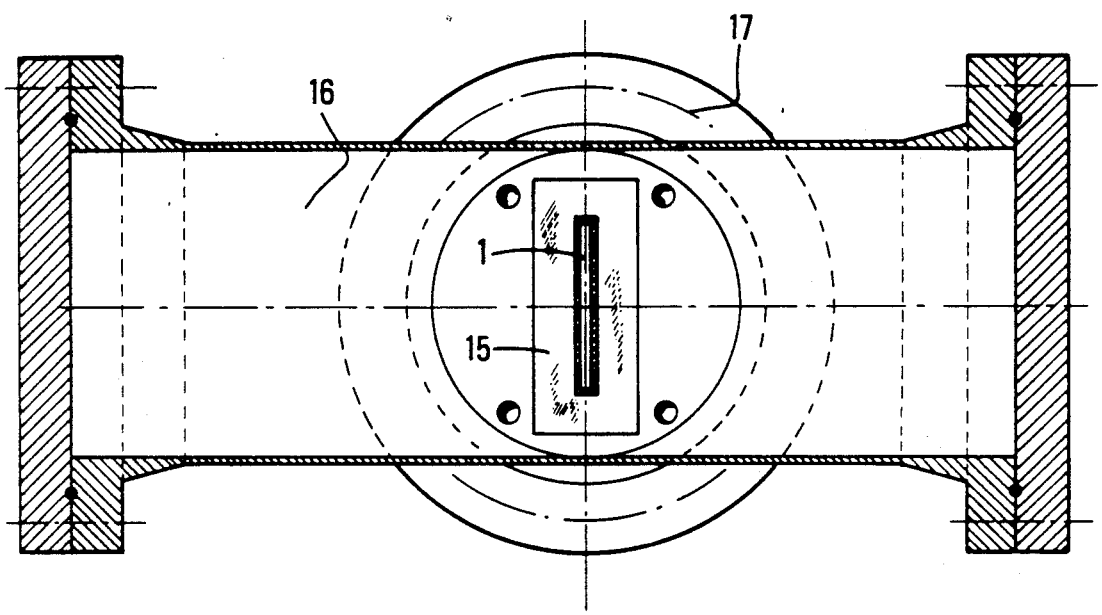

The invention will be better understood and its advantages will emerge clearly from reading the following description illustrated by the attached figures, wherein:

FIG. 1 shows schematically the operating principle of the measuring device according to the invention; and FIG. 2 illustrates a particular embodiment of the device in a cross section in the direction perpendicular to the fluid flow.

The diagram of FIG. 1 shows the operating principle of the device for measuring the qualities of a fluid flowing through a reinforced tube 1 which is connected both upstream and downstream to a diffuser 2 for transition from a circular cross section to a rectangular cross section, this diffuser having contant cross section, and a rectangular upstream converging section 3 or a rectangular downstream diverging section 4.

Upstream of a given point means the zone that an element of material (of the fluid) traverses during an industrial process before reaching the point in question, while on the contrary downstream means the zone reached after the point in question.

Upstream is to the left of the figure and downstream is to the right. The arrow in converging section 3 indicates the flow direction of the fluid.

Acquisition and processing of measurements may be broken down into several stages corresponding to separate measuring chains A, B, C, D, E, F. The elements of one measuring chain are reference by the same letter.

Chains A to E are measuring chains, using microwaves, each of which has a microwave transmitter 5, each of the transmitters transmitting at a given frequency or in a fixed frequency range, a microwave detector 6, which can be a microwave amplitude detector 6A, 6C or a microwave amplitude and frequency detector 6B, 6D, 6E, and an amplifier 7 of the signals of detector 6.

Chains B, C, E allow the velocity of the various fluid components to be measured by the Doppler effect. These chains in addition have an analyzer comparator 8 designed to compare the frequency of the amplified signal to the frequnecy of the signal emitted by transmitter 5 and possibly designed to perform a frequency analysis, for example to analyze a Fourier series, to determine the velocity of several fluids by shifts of the transmission frequency.

Chain A allows the water cross section in tube 1 to be determined by analyzing the absorption of the microwave flux at the frequency of 21 GHz.

Chain B allows the velocity of water in tube 1 to be determined by analyzing the shift in frequency of the microwave flux initially at the frequency 21 GHz.

The frequency of 21 GHz is chosen to isolate the behavior of the water. Once the water cross section and the velocity of the water are known, the volume flowrate of the water can be determined.

Chain C allows a relationship to be determined between the velocity of the water and the velocity of the oil by analyzing the frequency shifts of the microwave flux initially at a terminal frequency essentially between 35 and 80 GHz. Once this relationship is known, with the velocity of water known from chain B, the velocity of the oil can be determined.

Chain D allows the liquid (oil plus water) cross section in tube 1 to be determined by absorption analysis of the microwave flux at a terminal frequency between 35 and 80 GHz. From this, the oil velocity, the water cross-section measurement, and the oil cross-section the quantity of oil transported in the multiphase effluent can be deduced.

When the gas is completely separated from the liquids, chain E allows the velocity of the gas to be determined by a Doppler effect, from the particles entrained by the gas. The measurement is performed on the upper part of the flow, in which gas is found preferentially.

When the gas is dispersed within the liquid in the form of bubbles, the velocity of the gas is the same as the velocity of the liquids, disregarding the vertical component of the velocity, which is generally negligible relative to the horizontal component of the velocity.

When the gas passage cross section has been calculated from the difference between the fluid passage cross section in the tube and the passage cross sections of the water or oil previously determined, the volume flowrate of the gas is calculated by multiplying the passage cross section by the average velocity of the gas.

When the measurement are being made, it is preferable to dispose the tube in such a way that its lengthwise axis is horizontal and the longest dimension of its cross section is vertical, which is the case in FIG. 2 where the plane of the figure is vertical.

The type of flow with separated gas or bubbles inside the liquid can be determined by disposing a multiple chain E having a series of microwave sensors disposed velocity along the wall of the measuring section. The sensors would be of the second frequency type, sensitive only to the frequency of the liquids. The velocity of the free gas would be given only at the height corresponding to its presence in the measuring section. The information would be processed by a computer program.

Measuring chain F uses ultrasound to measure the density of the gas in the fluid, which is located in the upper part of the flow.

An ultrasound signal is transmitted by transmitter 9 and passes through a first wall in of tube 1, the gas, then a second wall of tube 1 before being detected by a sensor 10 furnishing an electrical signal amplified by amplifier 11. The ultrasound signal is transmitted in the form of a pulse, and comparator 12 allows the time necessary for propagation of the sound wave to be established, whereby this time depends on the density of the gas and the temperature value furnished by heat sensor 13. The mass flowrate of the gas can then be obtained from the volume flowrate, previously calculated, and the density.

All the information from measuring chains A to E and sensor 13 is processed by a computer 14 in order to furnish instant or cumulative values of the cross sections of the various fluids components at the velocity of these components.

Transmitters 5B, 5C, 5E, and detectors 6B, 6C, 6E are disposed respectively opposite each other, but their transmission or reception axis is inclined by 45° with respect to the flow axis in order to determine the velocity of the various components of the fluid.

Once the flowrate, temperature, and pressure (easy to obtain) are known, the density of the oil and water, and hence the mass flowrates of the oil and water, of an oil deposit, for example, can be determined by the PVT method used in the oil and chemical industries.

FIG. 2 illustrates a particular embodiment of the device according to the invention in cross section in the direction perpendicular to the fluid flow direction.

Tube 1, which appears in oblong rectangular form, is made of a material transparent to microwaves such as a resin-glass composite, and is resistant to the pressure differences between the inside and the outside of the pipe. This tube 1 is reinforced by ribs 15 disposed all around it at rectangular intervals. The rectangular shape of tube 1 was designed to permit natural separation of the gas and the liquids, and to allow correct measurement of the passage cross sections of the various liquids, since, when absorption is measured, it depends exponentially and nonlinearly on the thickness of the material traversed by the electromagnetic microwave flux (Beer-Lambert law).

The various transmitters and detectors are disposed along the tube between the ribs, and the other elements (amplifiers, analyzers, comparators) are disposed in a watertight tank 16 to allow immersion under the sea. This tank also allows the effluents to be contained if the measuring tube transparent to microwaves should deteriorate. Tube 1 has two flanges 17 for easy installation on a pipe.

In offshore oil production, tank 16 is connected to an electrohydraulic and electronic control module to provide the interface with the aforementioned computer which is at the surface of the sea.

The computer could also be built into the submerged tank, with the signals produced by the computer being multiplexed to be transmitted to the surface.

The measuring tube may be placed near an offshore production well in order to determine the composition of its effluent at the well outlet, as well as the flowrates of the effluents under local pressure and temperature conditions.

A nonlimitative embodiment of the method according to the invention will be indicated below.

Absorption and transmission of an electromagnetic wave, e.g. a microwave, through a sample, are governed by the Beer-Lambert law:

$$I = Io \times \exp(-Ka \cdot h) \text{ or } A = \log \frac{I}{Io} = \frac{-Ka \cdot h}{2.303}$$

where:
I = intensity of wave flux leaving the sample
Io = intensity of wave flux entering the sample
Ka = molar absorption factor of the material of which the sample is made
h = thickness of the sample
A = absorption.

Ka is a property of the sample material; it can be determined from the permittivity $\epsilon''$ in the complex plane. $\epsilon''$ is also called loss factor.

$$Ka = \frac{4\pi fVk}{c[C]} \text{ with } k = \frac{2n}{\epsilon''}$$

where:
f = measuring frequency
k = extinction coefficient
n = refractive index of sample material
V = volume fraction of sample material
c = velocity of electromagnetic waves in vacuum,
[C] = molar concentration of material in sample.
$\epsilon''$ varies according to frequency and is measurable.
The variations and amplitude of $\epsilon''$ depend on the type of material.

When total absorption $A_T$ is measured through walls (P) of a measuring tube, as described above, containing a fluid composed of water (W), oil (H), and gas (G), the sum of the absorptions of the components is measured, namely:

$$A_T = A_P + A_W + A_H + A_G.$$

If the total absorption $A_{T1}$ is measured at a frequency (index 1) of about 21 GHz (relaxation frequency of water), the water absorption will be vary large relative to that of the oil and gas, with the loss factors of water and oil being $\epsilon''_{W1}=40$ and $\epsilon''_{H1}=2\times 10^{-6}$, respectively.

Total absorption will be: $A_{T1}=A_{P1}+A_{W1}$.

If the total absorption $A_{T2}$ is measured at another frequency (index 2) for which the absorption contrast between the water and oil is small, for example at frequency $f_2=80$ GHz ($\epsilon''_{W2}=4$ and $\epsilon''_{H2}=2$) the absorption of the gas will still be negligible and hence $A_{T2}=A_{P2}+A_{W2}+A_{H2}$.

Since absorption $A_{P1}$ of the tube walls at frequency 1 has been measured previously, $A_{W1}$ is determined from the value of $A_{T1}$ and, since $Ka_{W1}$ or $\epsilon''_{W1}$ is known, the quantity of water or thickness of water $h_W$ can be determined by the relation:

$$A_{W1} = \frac{-Ka_{W1} \cdot h_w}{2.303}$$

Once the quantity of water is known, and with a measurement table available for the absorption coefficient of water Ka or loss factor $\epsilon''$ of water as a function of frequency, the absorption of water $A_{W2}$ at frequency 2 is determined.

Now that terms $A_{T2}$, $A_{P2}$, and $A_{W2}$ are known, $A_{H2}$ is determined by the formula:

$$A_{H2}=A_{T2}-A_{P2}-A_{W2}$$

and thus, since $Ka_{H2}$ or $\epsilon''_{H2}$ is known, we have the quantity of oil or thickness of oil $h_H$ $$h_H = \frac{-2.303 \cdot A_{H2}}{Ka_{H2}}$$

in the measuring section.

The quantity of gas in the measuring section is the volume not occupied by water or oil $h_G=h_T-(h_H+h_W)$, $h_T$ being the thickness of the measuring section.

Hence, the proportions of water, oil, and gas are defined respectively as follows:

$$h_W/h_T, h_H/h_T, h_G/h_T.$$

We claim:

1. A method of determining a quality of a fluid moving in a first direction within a tube means of known cross-section, the fluid including a first liquid and a second liquid, each liquid having a frequency-dependent intrinsic characteristic response to microwave energy, said method comprising the steps of:
   (a) passing microwave energy of a first frequency through the fluid-containing tube means in a second direction not perpendicular to the first direction, the first frequency being a frequency for which the value of the intrinsic characteristic of the first liquid is large in comparison to the value of the intrinsic characteristic of the second liquid and for which the value of the intrinsic characteristic of the tube means is known;
   (b) determining the value of the intrinsic characteristic of the microwave energy of the first frequency after passage thereof through the fluid-containing tube means;
   (c) determining the change in frequency of the microwave energy of the first frequency after passage thereof through the fluid-containing tube means;
   (d) passing microwave energy of a second frequency through the fluid-containing tube means in the second direction, the second frequency being a frequency for which the difference between the value of the intrinsic characteristic of the first liquid and the value of the intrinsic characteristic of the second liquid is small and for which the value of the intrinsic characteristic of the tube means is known;
   (e) determining the value of the intrinsic characteristic of the microwave energy of the second frequency after passage thereof through the fluid-containing tube means;
   (f) determining the change in frequency of the microwave energy of the second frequency after passage thereof through the fluid-containing tube means;
   (g) determining the cross-section of the first liquid within the tube means from the known value of the intrinsic characteristic of the tube means to the microwave energy of the first frequency and the result of step (b);
   (h) determining the cross-section of the combined first and second liquids within the tube means from the known value of the intrinsic characteristic of the tube means to the microwave energy of the second frequency and the result of step (e);
   (i) determining the velocity of the first liquid within the tube means from the result of step (c);
   (j) determining the relationship between the velocity of the first liquid and the velocity of the second liquid within the tube means from the result of step (f);
   (k) determining the cross-section of the second liquid within the tube means from the results of steps (g) and (h);
   (l) determining the velocity of the second liquid within the tube means from the results of steps (i) and (j);
   (m) determining the volume flow rate of the first liquid within the tube means from the results of steps (g) and (i); and
   (n) determining the volume flow rate of the second liquid within the tube means from the results of steps (k) and (l).

2. A method as claimed in claim 1, wherein the intrinsic characteristic is the absorption of microwave energy.

3. A method as claimed in claim 1 or 2, wherein step (b) includes neglecting the change in the intrinsic characteristic of the microwave energy of the first frequency due to the second liquid.

4. A method as claimed in claim 1, wherein the first liquid has an aqueous component, and wherein the first frequency is a frequency in the order of about 21 GHz and the second frequency is a frequency remote from 21 GHz.

5. A method as claimed in claim 1, wherein the fluid further includes a moving gas having particles with an intrinsic characteristic response to microwave energy, and wherein said method further comprises the steps of:
   (o) separating at least a part of the gas from the liquids;
   (p) passing microwave energy of a known frequency through the separated gas in the second direction, the known frequency being a frequency for which the value of the intrinsic characteristic of the tube means is known;

(q) determining the change in frequency of the last-named microwave energy after passage thereof through the separated gas;

(r) determining the cross-section of the gas from the known cross-section of the tube means and the result of step (h);

(s) determining the velocity of the gas within the tube means from the result of step (g); and (t) determining the the volume flow rate of the gas within the tube means from the results of steps (r) and (s).

6. A method as claimed in claim 5, wherein the intrinsic characteristic is the absorption of microwave energy.

7. A method as claimed in claim 5, wherein the first liquid has an aqueous component, and wherein the first frequency is a frequency in the order of about 21 GHz and the second frequency is a frequency remote from 21 GHz.

8. A method as claimed in claim 5, wherein the tube means includes a section having two parallel faces, and wherein each of step (a) and step (d) comprises passing microwave energy through the parallel faces.

9. A method of determining the volume flowrates of first and second liquids in a fluid moving in a first direction within a tube means of known cross-section, each liquid having a frequency-dependent absorption characteristic response to microwave energy, said method comprising the steps of:

(a) passing microwave energy of a first frequency through the fluid-containing tube means, the first frequency being a frequency for which the absorption characteristic of the first liquid is large in comparison with the absorption characteristic of the second liquid and for which the absorption characteristic of the tube is known;

(b) determining the absorption of the microwave energy of the first frequency by the first liquid during passage of the microwave energy of the first frequency through the fluid-containing tube means;

(c) passing microwave energy of the first frequency through the fluid-containing tube means in a second direction not perpendicular to the first direction;

(d) determining the change in frequency of the last-named microwave energy after passage threof through the fluid-containing tube means;

(e) passing microwave energy of a second frequency through the fluid-containing tube means, the second frequency being a frequency for which the difference between the absorption characteristic of the first liquid and the absorption characteristic of the second liquid is small and for which the absorption characteristic of the tube means is known;

(f) determining the absorption of the microwave energy of the second frequency by first and second liquids during passage of the microwave energy of the second frequency through the fluid-containing tube means;

(g) passing microwave energy of the second frequency through the fluid-containing tube means in the second direction;

(h) determining the change in frequency of the last-named microwave energy after passage thereof through the fluid-containing tube means;

(i) determining the cross-section of the first liquid within the tube means from the known absorption characteristic of the tube to the microwave energy of first frequency and the result of step (b);

(j) determining the velocity of the first liquid within the tube means from the result of step (d);

(k) determining the cross-section of the combined first and second liquids within the tube means from the known absorption characteristic of the tube means to the microwave energy of the second frequency and the result of step (f);

(l) determining the relationship between the velocity of the first liquid and the velocity of the second liquid from the result of step (h);

(m) determining the cross-section of the second liquid within the tube means from the results of steps (i) and (k);

(n) determining the velocity of the second liquid from the results of steps (j) and (l);

(o) determining the volume flowrate of the first liquid within the tube means from the results of steps (i) and (j); and (p) determining the volume flowrate of the second liquid within the tube means from the results of steps (m) and (n).

10. A method as claimed in claim 9, wherein step (b) includes neglecting the absorption of the microwave energy of the first frequency by the second liquid.

11. A method as claimed in claim 9, wherein the first liquid has an aqueous component, and wherein the first frequency is a frequency in the order of about 21 GHz and the second frequency is a frequency remote from 21 GHz.

12. A method as claimed in claim 9, wherein the fluid includes a moving gas having particles with an absorption characteristic to microwave energy, said method further comprising the steps of separating at least a part of the gas from the liquids, passing microwave energy of a known frequency through the separated gas; determining the change in frequency of the last-named microwave energy after passage through the gas; and determining the velocity of the gas from the last-named change in frequency.

13. A method as claimed in claim 9, wherein the tube means includes a section having two parallel faces, and wherein each of step (c) and step (e) comprises passing microwave energy through the parallel faces.

14. Apparatus for determining a quality of a fluid moving in a first direction, the fluid including a first liquid and a second liquid, each liquid having a frequency-dependent intrinsic characteristic response to microwave energy, said apparatus comprising:

(a) a tube member, having two parallel windows transparent to microwave energy and having a known cross-section, for passage of the moving fluid therethrough;

(b) first transmitting means for transmitting microwave energy of a first frequency through the tube member windows and the moving fluid; the first frequency being a frequency for which the value of the intrinsic characteristic of the first liquid is large in comparison to the value of the intrinsic characteristic of the second liquid and for which the intrinsic characteristic of the tube member windows is known;

(c) first determining means positioned to receive microwave energy from said first transmitting means after passage thereof through said tube member windows and the fluid, for determining the value of the cross-section of the first liquid within said tube member;

(d) second transmitting means for transmitting microwave energy of the first frequency through the tube member windows and the moving fluid in a second direction not perpendicular to the first direction;

(e) second determining means positioned to receive microwave energy from said second transmitting means after passage thereof through said tube member windows and the fluid, for determining the value of the velocity of the first liquid within said tube member;

(f) third transmitting means for transmitting microwave energy of a second frequency through the tube member windows and the moving fluid in the second direction; the second frequency being a frequency for which the difference between the value of the intrinsic characteristic of the first liquid and the value of the intrinsic characteristic of the second liquid is small and for which the value of the intrinsic characteristic of the tube member windows is known;

(g) third determining means positioned to receive microwave energy from said third transmitting means after passage thereof through said tube member windows and the fluid, for determining the relationship between the velocity of the first liquid and the velocity of the second liquid within said tube member;

(h) fourth transmitting means for transmitting microwave energy of the second frequency through the tube member windows and the moving fluid;

(i) fourth determining means positioned to receive microwave energy from said fourth transmitting means after passage thereof through said tube member windows and the fluid, for determining the value of the cross-section of the combined first and second liquids within said tube member;

(j) computing means, coupled to said first, second, third, and fourth receiving means and said second and third transmitting means, and responsive to the determined values and relationship for computing the volume flowrates of the first and second liquids.

15. Apparatus as claimed in claim 14, wherein said tube member windows are made of a composite material.

16. Apparatus as claimed in claim 14, wherein said tube member is a section of pipe.

17. Apparatus as claimed in claim 14, wherein the first frequency is a frequency in the order of about 21 GHz and the second frequency is a frequency remote from 21 GHz.

* * * * *